United States Patent
Lyster et al.

(10) Patent No.: US 6,304,783 B1
(45) Date of Patent: Oct. 16, 2001

(54) DEFIBRILLATOR SYSTEM INCLUDING A REMOVABLE MONITORING ELECTRODES ADAPTER AND METHOD OF DETECTING THE MONITORING ADAPTER

(75) Inventors: Thomas D Lyster, Bothell; Daniel J Powers, Issaquah; Jon M Bishay, Woodinville, all of WA (US)

(73) Assignee: Heartstream, Inc., Seattle, WA (US)

( * ) Notice: Subject to any disclaimer, the term of this patent is extended or adjusted under 35 U.S.C. 154(b) by 0 days.

(21) Appl. No.: 09/418,538

(22) Filed: Oct. 14, 1999

(51) Int. Cl.[7] ................................................. A61N 1/39
(52) U.S. Cl. .................................................. 607/63
(58) Field of Search ................................. 607/27, 28, 63, 607/142

(56) References Cited

U.S. PATENT DOCUMENTS 4,850,356 * 7/1989 Heath .
5,562,710 * 10/1996 Olsen et al. .
5,591,213 1/1997 Morgan .
5,607,454 3/1997 Cameron et al. .
5,735,879 4/1998 Gliner et al. .
5,800,460 9/1998 Powers et al. .

* cited by examiner

Primary Examiner—Scott M. Getzow
(74) Attorney, Agent, or Firm—Matthieu van Kaam; Tony E. Piotrowski; Graybeal Jackson Haley LLP

(57) ABSTRACT

A defibrillator system capable of defibrillation and patient monitoring. When used as a patient monitor, the defibrillator system includes a defibrillator and removable monitoring electrodes. The monitoring electrodes communicate with a monitoring adapter and the defibrillator. A method of detecting the presence of the monitoring electrodes by the defibrillator is also included. A removable monitoring adapter. The removable monitoring adapter having a test impedance. Defibrillators include semi-automatic defibrillators and automatic defibrillators ("AEDs").

20 Claims, 5 Drawing Sheets

DEFIBRILLATOR SYSTEM INCLUDING A REMOVABLE MONITORING ELECTRODES ADAPTER AND METHOD OF DETECTING THE MONITORING ADAPTER

BACKGROUND OF THE INVENTION

1. Field of the Invention

This invention relates generally to a defibrillator system which is capable of defibrillation and patient monitoring. When used as a patient monitor, the defibrillator system includes a defibrillator, removable monitoring adapter, and monitoring electrodes. Monitoring electrodes communicate with the monitoring adapter and the defibrillator, providing means to observe the patient's electrocardiogram ("ECG"). A method of detecting the presence of the monitoring adapter by the defibrillator is also included. This invention also relates to the removable monitoring adapter. Defibrillators include manual defibrillators, semi-automatic defibrillators and automatic defibrillators. Semi-automatic defibrillators and automatic defibrillators are collectively referred to as "AEDs."

2. Description of the Prior Art

Sudden cardiac arrest ("SCA") is the leading cause of death in the United States. Most sudden cardiac arrest is caused by ventricular fibrillation ("VF"), in which the heart's muscle fibers contract without coordination, thereby interrupting normal blood flow to the body. The only known effective treatment for VF is electrical defibrillation, in which an electrical pulse is applied to the patient's heart. The electrical pulse must be delivered within a short time after onset of VF in order for the patient to have any reasonable chance of survival. Electrical defibrillation may also be used to treat pulseless ventricular tachycardia ("VT"). Accordingly, defibrillation is the appropriate therapy for any shockable rhythm, i.e., VF or pulseless VT.

One way of providing electrical defibrillation uses an external defibrillator. External defibrillators send electrical pulses to the patient's heart through electrodes applied to the patient's torso. External defibrillators are typically located and used in hospital emergency rooms, operating rooms, and in emergency medical vehicles. Of the wide variety of external defibrillators currently available, AEDs are becoming increasingly popular because they can be used by relatively inexperienced personnel. AEDs are also especially lightweight, compact and portable. AEDs are described, for example, in U.S. Pat. No. 5,607,454 to Cameron et al. entitled "Electrotherapy Method and Apparatus" and U.S. Pat. No. 5,591,213 to Morgan entitled "Defibrillator System Condition Indicator," the specifications of which are incorporated herein.

One example of a defibrillator that provides a mechanism for detecting monitoring electrodes is the Laerdal HeartStart 3000. The Heartstart 3000 measures impedance through the electrodes attached to the patient to determine whether the monitoring pads are attached. The HeartStart 3000 distinguishes between the patient and monitoring electrodes by establishing an impedance threshold for which patient impedances are on one side of the threshold and monitoring electrode impedances are on the other side of the threshold.

AEDs provide a number of advantages, including the availability of external defibrillation at locations where external defibrillation is not regularly expected, and is likely to be performed quite infrequently, such as in residences, public buildings, businesses, personal vehicles, public transportation vehicles, etc. However, many instances of symptomatic patients may occur where defibrillation is not required, or formally permitted, because the patient is not suffering SCA and does not meet the indications for use of an AED. Some AEDs could be used to monitor the patient's ECG using the defibrillation electrodes, but these electrodes are expensive and could represent some risk to a patient who doesn't need defibrillation. Yet, traditional low cost monitoring electrode are not appropriate, because most AEDs are not configured to detect or operate with monitoring electrodes.

What is needed is a simple, low cost and effective way of providing an ECG monitoring function in an AED, while ensuring that the AED does not attempt to send a defibrillation energy pulse through the monitoring electrodes.

SUMMARY OF THE INVENTION

This invention provides a defibrillator system for monitoring or defibrillating a patient, comprising: a defibrillator capable of delivering an electrical pulse to the patient; and a removable monitoring adapter in communication with the defibrillator and a set patient sensors, wherein the monitoring adapter is operable to communicate a patient parameter to the defibrillator, and enable detection of the monitoring adapter by the defibrillator, when the adapter is connected to the defibrillator. An important feature of the invention is that the defibrillator inactivates the defibrillation capability in response to detection of the adapter. The defibrillator detects the adapter based on the interface impedance of the adapter measured by the defibrillator. Specifically, the defibrillator detects the adapter based on the imaginary impedance of the adapter interface greater than zero, measured by the defibrillator. Additionally, the adapter may also be capable of identifying a fault condition to the defibrillator. Typically fault systems that are detected by the system include: low battery condition and disconnected sensors. The monitoring adapter may be configured to removably connect with sensors, such as monitoring electrodes. Alternatively, the adapter may be configured so that the monitoring electrodes are integral with the monitoring device. In a preferred embodiment, the ECG monitoring electrodes also function as a right-leg drive. The monitoring electrode system can include from 2–12 electrodes.

A monitoring adapter is provided that communicates a patient parameter to a medical device which enables detection of the monitoring adapter, when the adapter is connected to the medical device. As a result of detection of the adapter, operation of the medical device is changed. Detection of the adapter is enabled based on the interface impedance of the adapter measured by the medical device. The medical device is a defibrillator and the monitoring adapter communicates with the defibrillator a set of ECG monitoring electrodes. In one specific embodiment, the monitoring adapter is formed integral with the monitoring electrode pads. Alternatively, the monitoring adapter may be configured so that it is removably connected to electrode pads. A fault detector may also be provided within the monitoring adapter to detect a fault condition. The monitoring electrode system can include from 2–12 electrodes.

A monitoring electrode system for use with a defibrillator, comprising: a set of monitoring electrodes; a test impedance, wherein the monitoring detector increases the impedance seen by the a defibrillator to a value greater than would occur in the absence of the monitoring detector. The monitoring electrode system can include from 2–12 electrodes. Typically, the monitoring adapter communicates with a defibrillator a set of monitoring electrode pads. In one embodiment, the monitoring electrode system is formed such that the monitoring adapter is integral with the monitoring electrode pads. Alternatively, the monitoring adapter is removably connectable to monitoring electrode pads. The system may also include a fault detector.

This invention also relates to a method of identifying the presence of a monitoring adapter comprising: measuring impedance at a patient connector. In measuring impedance, the device determines: if the ratio of $Z_i/Z_r$ is greater than a first threshold, then the monitor adapter is present; or if the ratio of $Z_i/Z_r$ is less than or equal to the first threshold, then the monitor adapter is not present. In the event the monitor adapter is not present, normal device functionality is enabled. However, if the monitor adapter is present, monitoring device functionality is enabled. In determining whether a fault condition exists, the device looks at $Z_i$. If $Z_i$ is greater than a second threshold, a fault condition is present, or if $Z_i$ is less than the second threshold, a fault condition is not present. Fault conditions include, for example, leads off, circuit fault, or battery fault.

Another method practiced under this invention is that of identifying the presence and state of a monitoring adapter comprising: measuring complex impedance at a connector wherein the connector is connected to the adapter.

Yet another method practice under this invention is that of identifying the presence of a monitoring adapter comprising: measuring impedance at a patient connector or at the device.

DESCRIPTION OF THE PREFERRED EMBODIMENTS

The following discussion is presented to enable a person skilled in the art to make and use the invention. Various modifications to the preferred embodiment will be readily apparent to those skilled in the art, and the generic principles herein may be applied to other embodiments and applications without departing from the spirit and scope of the present invention as defined by the appended claims. Thus, the present invention is not intended to be limited to the embodiment show, but is to be accorded the widest scope consistent with the principles and features disclosed herein.

Figure 1:
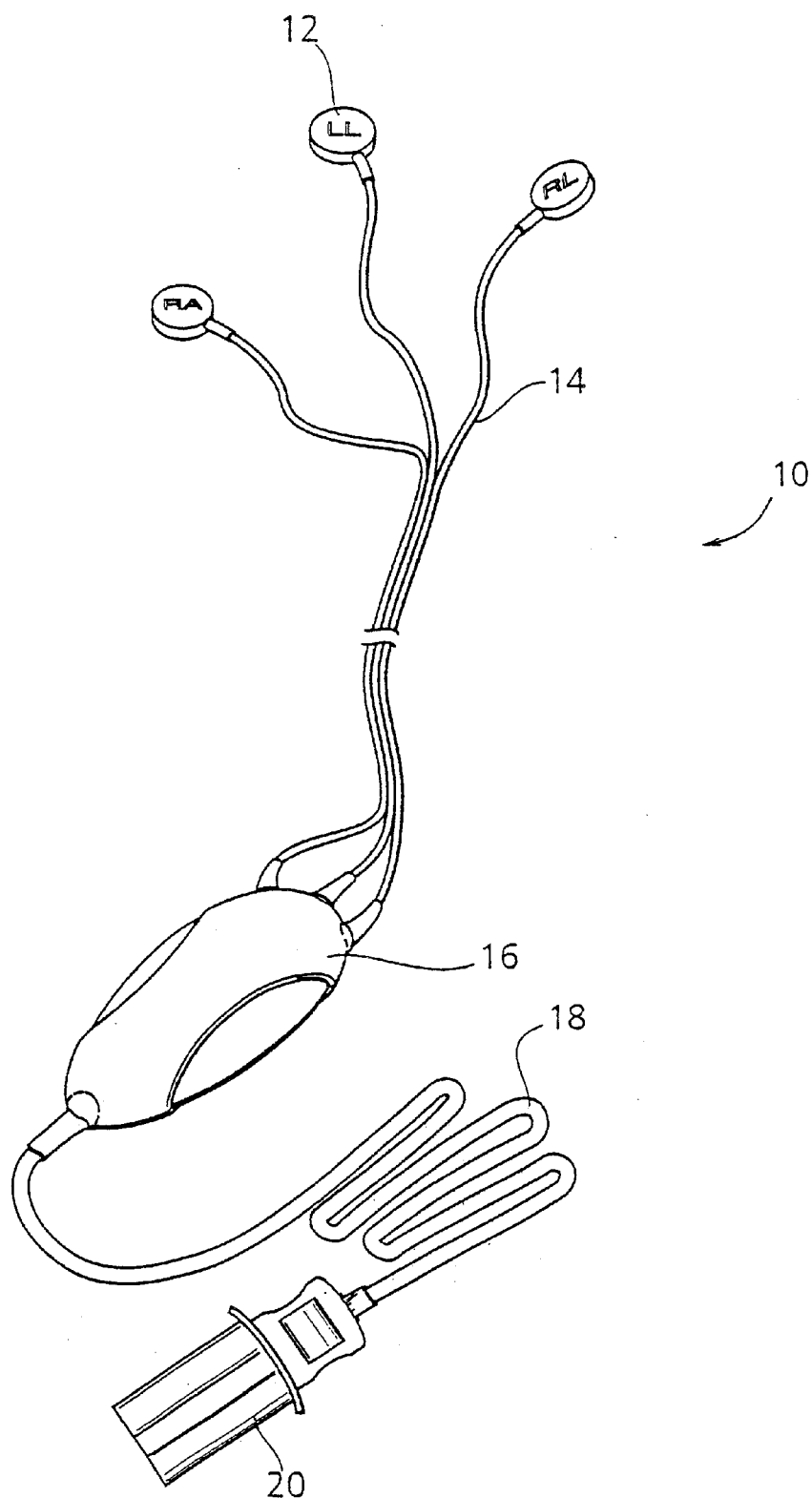
FIG. 1 is an elevated plan view of an adapter according to this invention.

FIG. 1 illustrates a removable monitoring adapter system 10. The adapter features a set of monitoring electrode connectors 12. The configuration shown in FIG. 1 shows three monitoring electrode connectors RA, LL and RL typical of the configuration used in connection with a right leg drive monitoring configuration. Each of the three electrode connectors 12 are connected to an adapter 16 via connection wires 14. As will be appreciated by persons of skill in the art, the connection wires may associate with the adapter 16 separately (as shown) or may be configured such that they form a single wiring bundle. Disposable monitoring electrodes (not shown) are connected to the electrode connectors 12. Disposable monitoring electrodes could be attached, for example, by means of a snap connector or a clamp. Suitable electrodes include, for example, 3M Red Dot monitoring electrodes. Additional, other connection means may also be provided without departing from the scope of the invention. As will be appreciated by those of skill in the art, monitoring electrode pads could also be formed integral with the adapter system 10. However, in such an instance the cost benefit associated with using disposable electrodes may be subverted if the integrated monitoring electrodes are not reusable. Additionally, the adapter system 10 may be configured to have more or fewer electrodes. Typically, the adapter would be configured to have between 2–12 electrode connectors.

The adapter 16 contains circuitry, discussed in more detail below, that enables the defibrillator to identify the presence of the adapter, thus configuring the defibrillator to monitor ECG and prohibit delivery of a defibrillation shock. In this embodiment, adapter 16 is connected to a connector 20 via a wire 18. Connector 20 provides a standard two wire connection to the defibrillator. Although the adapter 16 and the connector 20 are shown in FIG. 1 as being separated by wire 18, it will be appreciated by those of skill in the art that the functionality of adapter 16 could be incorporated into connector 20, thereby eliminating wire 18 without departing from the scope of the invention. Additionally, the adapter 16 could be a removable reusable adapter. In that instance, the monitoring electrodes 12 would plug into the adapter 16 and the adapter 16 would, in turn, plug into the defibrillator.

Figure 2:
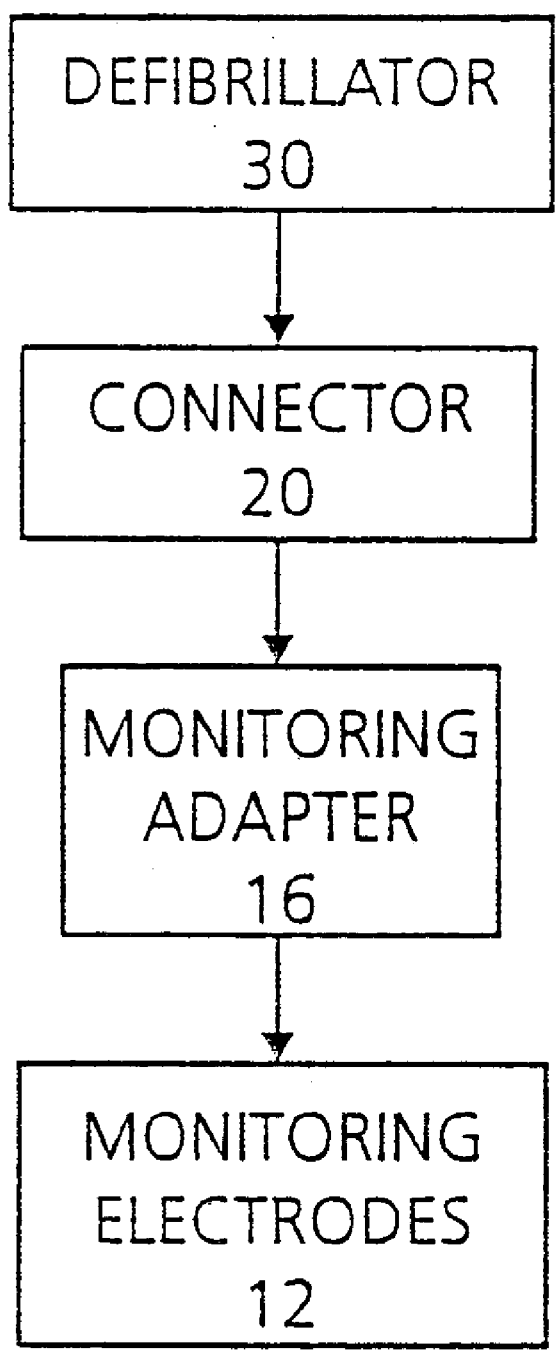
FIG. 2 is a functional block diagram depicting a defibrillator connected to monitoring electrodes.

Turning to FIG. 2, a high level block diagram is depicted that illustrates the defibrillator 30 connected to monitoring electrodes 12 via a connector 20 and monitoring adapter 16. Although depicted as separate blocks, as discussed above, connector 20 and monitoring adapter 16 may be formed integrally as mentioned above.

Figure 3:
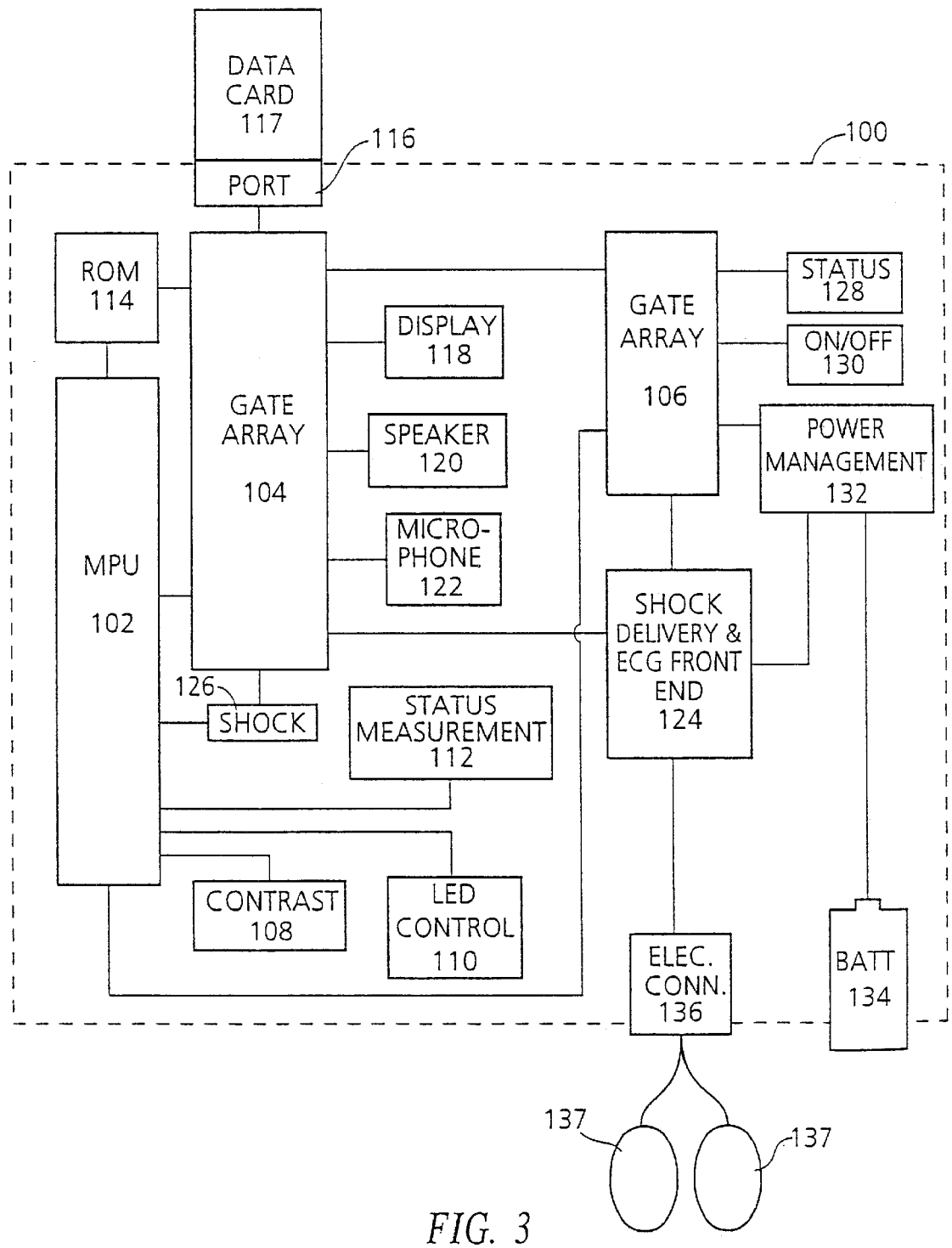
FIG. 3 is a block diagram of an AED suitable for use in this invention.

The major components of an AED 100 suitable for use in conjunction with this invention are shown in FIG. 3 in block diagram form. In this example, AED 100 control functions are divided among a microprocessor unit (MPU) 102 and two custom gate arrays 104 and 106. It should be understood, however, that gate arrays 104 and 106 are optional, and their functions can be performed by other circuits.

MPU 102 performs program steps according to software instructions provided to it from ROM 114. MPU 102 controls the operation of certain buttons (such as display contrast buttons 108) and certain system LED's 110 (such as LED's associated with the shock button and the electrode connector). MPU 102 receives system status information as shown by block 112. MPU 102 also controls the operation of the display contrast button 108.

As shown in FIG. 3, gate array 104 implements a memory map to system ROM 114, data card port 116 and other system memory elements.

Gate array 106 provides a system monitor function by initiating automatic self-tests of the defibrillator and its components. The gate array 106 displays the operational status of the defibrillator on a status display 128. Gate array 106 is also the defibrillator's interface with a user-activated on/off switch 130.

Gate array 106 also may control the power management subsystem 132 to provide power to operate system components from battery 134 and to provide energy to the shock delivery system's capacitor(s) for a therapeutic shock during treatment mode. Power management subsystem 132 enables energy from the battery 134 to be delivered to the patient 18 via shock delivery and ECG front end 124. For that purpose, power management subsystem 132 includes a capacitor (not shown). Gate array 106 also interfaces with the defibrillator's ECG front end 124, providing data to the MPU, which performs detection of a patient ECG pattern requiring treatment. The gate array 106 also controls delivery of the shock to electrode connector 136, upon actuation of the shock button, in response to shock delivery status information obtained during delivery of the shock.

The front end 124 provides for an impedance measurement to be made by MPU 102, via connector 136. For example, a preliminary fixed current waveform is delivered to the connector 136. A suitable signal would be, for example, a 540 Hz signal. A return signal is received by the defibrillator front end 124, and delivered to MPU 102, which calculates the impedance present at connector 136. By analyzing the impedance, MPU 102 can determine if the monitoring adapter is present at connector 136, and select software instructions from ROM 114 which configures the defibrillator as a monitor only, thus suppressing the defibrillation function. When MPU 102 determines that the adapter is present, MPU 102 can also determine if monitoring electrodes are disconnected from the patient.

If the impedance analysis determines that the monitor adapter 16 is not present, then the standard software instructions are selected and the AED functions normally. Further information regarding defibrillator operation be found in U.S. Pat. No. 5,735,879 by Gliner et al. for "Electrotherapy Method for External Defibrillators" and U.S. Pat. No. 5,607,454 by Cameron et al. for "Electrotherapy Method and Apparatus," the disclosures of which are incorporated herein by reference.

As is known in the art, the AED 100 can be operated in different modes, such as self-test mode, stand-by mode and patient treatment mode. Further discussion of the operation of an external defibrillator in self-test mode, stand by mode and patient treatment mode is provided in U.S. Pat. No. 5,800,460 by Powers et al. for "Method for Performing Self-Test in a Defibrillator", the specification of which is incorporated herein.

Figure 4:
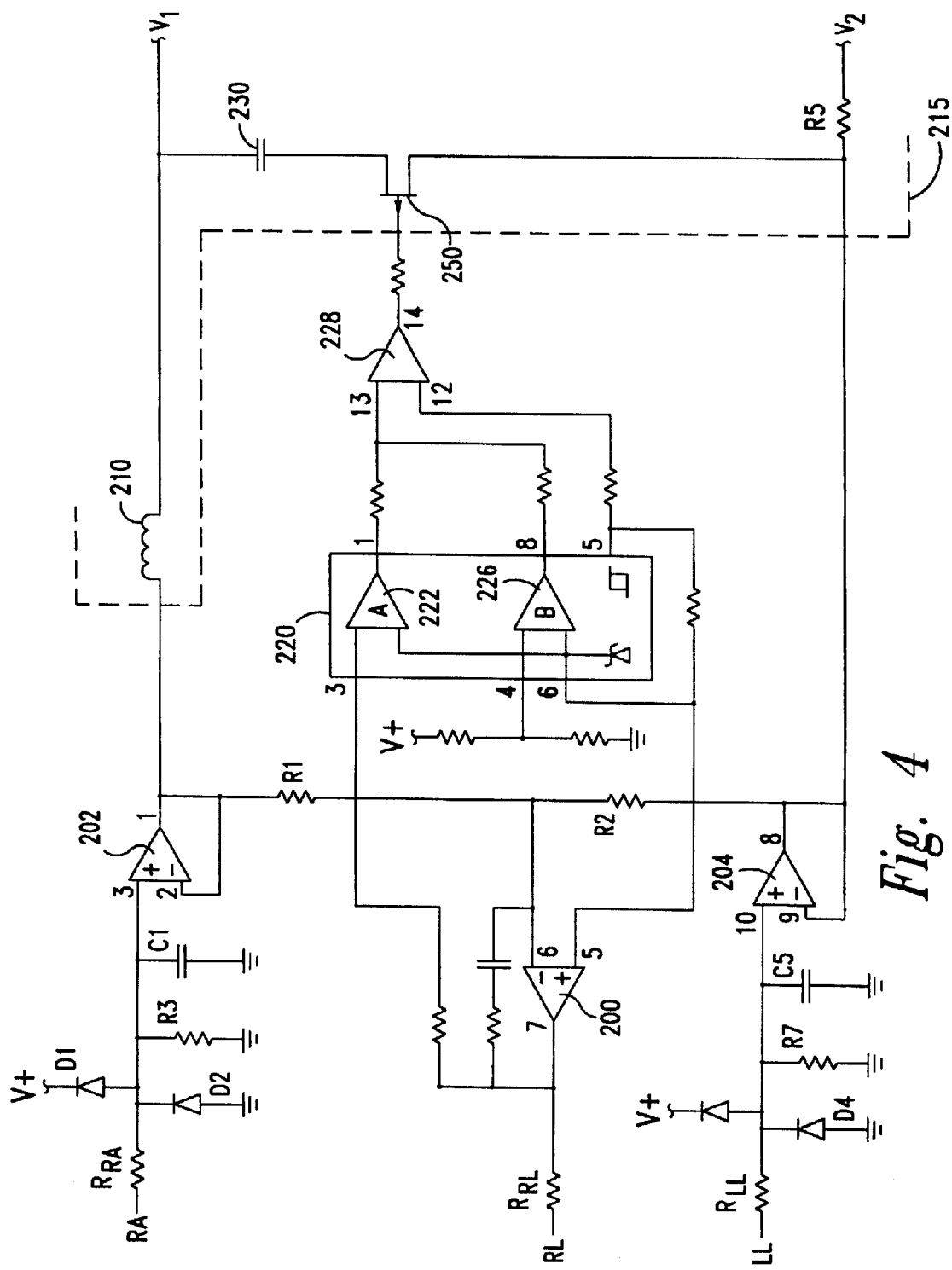
FIG. 4 is a schematic diagram showing a circuit that enables the AED to detect the presence of monitoring adapter and to detect disconnected electrodes.

FIG. 4 illustrates a circuit implementation of the monitor adapter, which includes a right leg drive system similar to that which is commonly known in the art. Typically modern electrocardiographic systems do not ground the patient. In order to overcome the interference effects of large common mode signals present on an un-grounded patient the right-leg electrode is connected to the output of an auxiliary op amp 200, which effectively shunts the common mode currents away from sense electrodes RA and LL. The common-mode voltage on the body is derived by averaging the signals present at RA and LL, via the output of unity gain amplifiers 202 and 204, with resistors $R_1$ and $R_2$. This average is inverted, amplified and fed back to the right leg, RL, via the output of the auxiliary op amp 200 through resistor $R_{RL}$. Bias voltage of 1.18 V is also established for amplifiers 202 and 204 via this feedback path. The negative feedback then drives the common-mode voltage on the body to a low value, thus minimizing the interference in the patient's ECG. Resistor $R_{RL}$ is located in series between the patient and the op amp 200 which, in the event of an abnormally high voltage, would limit the current to a safe level.

Op amps 202 and 204 buffer the ECG signal received via RA and LL, providing a low impedance unity gain ECG signal for the AED at V1 and V2. Input resistors $R_{RA}$ and $R_{LL}$ and diodes ($D_1$, $D_2$, $D_3$ and $D_4$) protect op amps 202 and 204 against high voltage transients that might be present, such as the presence of another defibrillator. Capacitors $C_1$ and $C_3$ provide high-frequency filtering of the input signal received from RA and LL. Resistors $R_3$ and $R_7$ provide a bias current which will drive the amplifier outputs of op amps 202 and 204 to ground if an electrode is removed from the patient.

Inductor 210, resistor $R_5$, capacitor 230, and switch 250, present a unique impedance interface 215 at $V_1$, $V_2$, which enables the AED to detect the presence of the monitor adapter, as well as disconnected electrodes RA, RL, or LL. Interface 215 presents significant inductive reactance and resistance to the AED. When the AED is connected to a patient using defibrillation electrode pads, under normal conditions, the patient impedance presents a distinctly different impedance, including capacitive reactance and much lower resistance, than the monitor adapter. Thus, the AED can be configured to operate in either normal defibrillation mode or monitor mode only, depending on the impedance measured at the patient connector.

In a preferred embodiment the inductor 210 is 470 mH, capacitor 230 is 0.12 µF, and resistor $R_5$ is 3.4 kΩ. When the monitor adapter is connected to the AED then the following impedance relationships measured by the AED shall hold (where a small-signal 540 Hz impedance data is analyzed to indicate the device):

| Adapter state | Adapter present | Leads on | Leads off |
|---|---|---|---|
| Impedance (Ω) | $Z_i/Z_r > .25$<br>$Z_r > 2000$<br>$Z_r < 10000$ | $Z_i < 2200$ | $Z_i \geq 2200$ |

Where $Z_r$ is the real impedance sample.
Where $Z_i$ is the imaginary impedance sample.

When the adapter is present and the leads are connected to the patient, then switch 250 disconnects capacitor 230 from the interface and the AED measures a 3.4 kΩ resistor in series with inductor 210, thus meeting the impedance requirements for an adapter connected with all leads on the patient. The J-FET switch 250 in series with a capacitor 230 together function as an electrode disconnect and battery fault encoder for the monitor impedance. In the event a lead is off, or a battery fault condition occurs, J-FET 250 is switched to a low resistance state, thus connecting capacitor 230 in parallel with inductor 210. The capacitor 230 causes the inductive reactance to increase as seen by the defibrillator, thus meeting the impedance requirements for an adapter with one or more leads off.

Comparator 220 and op amp 228 form the logic and control for switch 250, which enables the leads off and battery fault function. If the battery is low, or any of the leads are disconnected, then comparator 220 drives the inverting input of op amp 228 high, thus driving the gate of J-FET switch 250 low, which in turn causes low switch resistance. Logic 220 includes voltage comparators 222a and 222b and zener diode 224. Zener diode 224 sets the reference voltage for the system.

Figure 5:
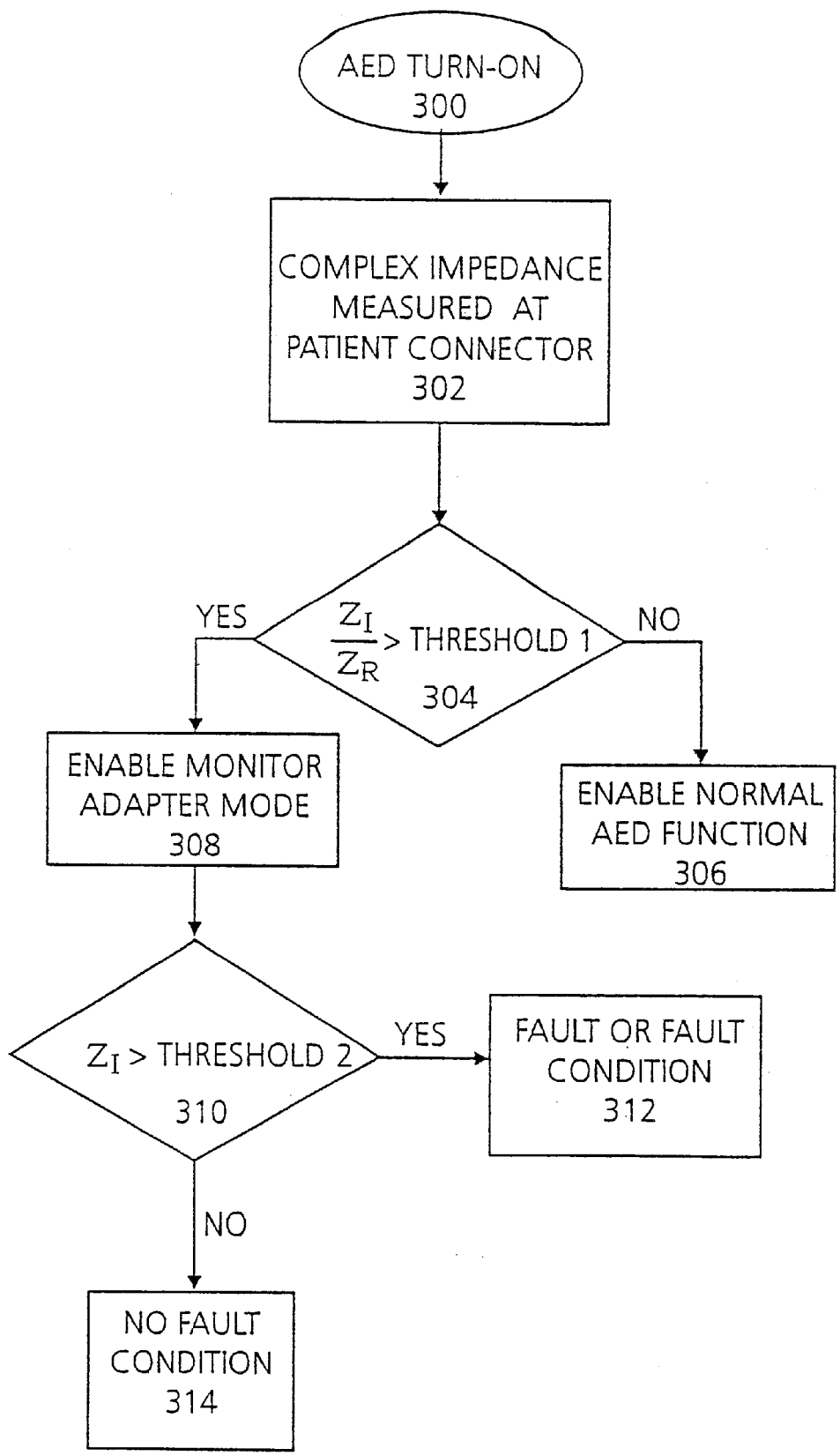
FIG. 5 is a flow chart demonstrates the method of identification of the adapter by the defibrillator.

In FIG. 5, defibrillator measures the complex impedance at the patient connector by delivering a current signal to the connector and measuring the resulting voltage signal. When the defibrillator is directly connected to a patient, the impedance measured by the defibrillator meets the normal resistive operating requirements, and the defibrillator functions normally. In contrast, when the defibrillator is used in conjunction with the adapter 16 (connected in series with monitoring electrodes 12 or integral with the monitoring electrodes, as shown in FIG. 1), the impedance signal measured by defibrillator meets the monitoring adapter detection requirements, which include inductive reactance, $Z_i$, and high resistance, $Z_r$. Thus the defibrillator is reconfigured as a passive monitor suppressing the shock capability of the defibrillator.

Turning to the specifics of FIG. 5 which describes a method for using the adapter in conjunction with an AED. The first step is to turn the AED on 300. Next, a complex impedance is measured, for example, at the patient connector 302. If $Z_I/Z_R$ is greater than threshold 1 304 then the monitoring mode is enabled 308. If $Z_I/Z_R$ is less than or equal to threshold 1 304 then the monitoring mode is not enabled 306. Once monitoring mode is enabled, it is determined whether $Z_I$, is greater than threshold 2 310. If $Z_I$, is greater than threshold 2 then a fault or fault condition 312 exists. If $Z_I$ is not greater than threshold 2, then no fault or fault condition exists. Examples of values for $Z_I$ is provided in more detail above.

Modifications to the invention embodiments described above will be apparent to those skilled in the art. Such modifications are within the scope the invention.

What is claimed:

1. A defibrillator system for monitoring or defibrillating a patient, comprising:
    a defibrillator capable of delivering an electrical pulse to the patient; and
    a removable monitoring adapter in communication with the defibrillator and a set of patient sensors, the monitoring adapter operable to communicate a patient parameter to the defibrillator and enable detection of the monitoring adapter by the defibrillator when the monitoring adapter is connected to the defibrillator,
    wherein the defibrillator inactivates a defibrillation capability in response to detection of the monitoring adapter.

2. A defibrillator system according to claim 1 wherein the defibrillator detects the adapter based on the interface impedance of the adapter measured by the defibrillator.

3. The defibrillator system according to claim 1 wherein the defibrillator detects the adapter based on the imaginary impedance of the adapter interface greater than zero, measured by the defibrillator.

4. The defibrillator system according to claim 1 wherein a fault condition detector within the adapter identifies a fault condition to the defibrillator.

5. The defibrillator system according to claim 4 wherein the fault conditions are selected from the group consisting of: low battery condition and disconnected sensors.

6. The defibrillator system according to claim 1 wherein the monitoring adapter is integral with the monitoring sensors.

7. The defibrillator system according to claim 1, wherein the sensors are comprised of ECG electrodes.

8. The defibrillator system according to claim 7, wherein one of the ECG electrodes functions as a right leg drive.

9. The defibrillator system of claim 7, wherein the defibrillator system communicates with a plurality of patient sensors.

10. In a medical device capable of performing a default function upon a patient, a method of identifying the presence of a monitoring adapter comprising the steps of:
    measuring impedance at a patient connector to determine whether the monitoring adapter is present; and
    inactivating the default function in the event that the monitoring adapter is present.

11. The method of claim 10, wherein:
    if a complex impedance is greater than a first threshold, then the monitor adapter is present, or
    if a complex impedance is less than or equal to the first threshold, then the monitor adapter is not present.

12. The method of claim 11 wherein if the monitor adapter is present, monitoring device functionality is enabled.

13. The method of claim 11, wherein:
    if an imaginary portion of a complex impedance is greater than a second threshold, a fault condition is present, or
    if an imaginary portion of a complex impedance is less than the second threshold, a fault condition is not present.

14. The method of claim 13, wherein the fault condition is selected from the group consisting of: leads off, circuit fault, and battery fault.

15. The method of claim 11, wherein if the monitoring adapter is not present the default function is enabled.

16. A monitoring adapter operable to communicate a patient parameter to and enable detection by a medical device, comprising:
    a common mode shunt circuit;
    a sense electrode circuit coupled to the common mode shunt circuit;
    a comparator coupled to the common mode shunt circuit; and
    a switched impedance interface coupled to the comparator circuit and the sense electrode circuit,
    wherein the common mode shunt circuit and the sense electrode circuit may be selectively coupled to a patient.

17. A medical system for selectively performing a default function upon or monitoring a patient, comprising:
    a medical device capable of performing the default function; and
    a removable monitoring adapter operable to communicate a patient parameter to and enable detection by the medical device when coupled to the medical device,
    wherein the medical device disables the default function in response to detecting the monitoring adapter.

18. The medical system of claim 17, wherein the medical device detects the monitoring adapter based upon a measurement of a complex interface impedance.

19. The medical system of claim 18, wherein the fault detector comprises a switch coupled to a capacitor.

20. The medical system of claim 17, wherein the monitoring adapter comprises patient monitoring circuitry and a fault detector.

* * * * *